United States Patent
Andersson et al.

(10) Patent No.: US 12,296,189 B2
(45) Date of Patent: May 13, 2025

(54) COMPUTER-IMPLEMENTED METHOD FOR RADIOTHERAPY TREATMENT PLANNING, COMPUTER PROGRAM PRODUCT AND COMPUTER SYSTEM FOR PERFORMING THE METHOD

(71) Applicant: RaySearch Laboratories AB (Publ), Stockholm (SE)

(72) Inventors: Bjorn Andersson, Uppsala (SE); Erik Engwall, Hagersten (SE); Albin Fredriksson, Stockholm (SE); Kjell Eriksson, Balsta (SE)

(73) Assignee: Raysearch Laboratories AB (publ), Stockholm (SE)

( * ) Notice: Subject to any disclaimer, the term of this patent is extended or adjusted under 35 U.S.C. 154(b) by 266 days.

(21) Appl. No.: 17/907,546

(22) PCT Filed: Mar. 22, 2021

(86) PCT No.: PCT/EP2021/057253
§ 371 (c)(1),
(2) Date: Sep. 28, 2022

(87) PCT Pub. No.: WO2021/197893
PCT Pub. Date: Oct. 7, 2021

(65) Prior Publication Data
US 2023/0144962 A1     May 11, 2023

(30) Foreign Application Priority Data

Apr. 2, 2020 (EP) .................................... 20167796

(51) Int. Cl.
*A61N 5/10* (2006.01)
(52) U.S. Cl.
CPC ........... *A61N 5/1001* (2013.01); *A61N 5/103* (2013.01); *A61N 5/1038* (2013.01)

(58) Field of Classification Search
CPC .... A61N 5/1001; A61N 5/103; A61N 5/1038; A61N 5/1031; A61N 5/1077
See application file for complete search history.

(56) References Cited

U.S. PATENT DOCUMENTS

| 5,716,595 A | * | 2/1998 | Goldenberg | ............ | A61P 29/00 |
| | | | | | 424/1.49 |
| 6,096,289 A | * | 8/2000 | Goldenberg | ............ | B82Y 5/00 |
| | | | | | 424/1.49 |

(Continued)

FOREIGN PATENT DOCUMENTS

| CN | 105792894 A | 7/2016 |
| EP | 3055024 A1 | 8/2016 |

(Continued)

OTHER PUBLICATIONS

First office action in China dated Apr. 28, 2024, Chinese Patent Office, China.

(Continued)

*Primary Examiner* — David P Porta
*Assistant Examiner* — Gisselle M Gutierrez
(74) *Attorney, Agent, or Firm* — Noréns Patentbyrå Ab

(57) ABSTRACT

A computer-based method of optimizing a radiotherapy treatment plan for a patient is proposed, wherein a complete treatment comprising both external beam therapy and brachytherapy is optimized in one procedure using an optimization problem comprising an objective function designed to optimize the total dose distribution as a combination of a first dose distribution to be provided by a first radiation set and a second dose distribution to be provided by a second radiation set. One of the radiation sets is external beam radiotherapy and the other is brachytherapy. The optimization is based on a total desired dose for the whole treatment, images of the patient before the treatment starts (Continued)

and an estimated image of the patient after the first radiation set has been delivered.

11 Claims, 2 Drawing Sheets

(56) References Cited

U.S. PATENT DOCUMENTS

| | | | |
|---|---|---|---|
| 9,744,379 B2* | 8/2017 | Bharat | G10L 21/0208 |
| 2011/0130614 A1 | 6/2011 | Schulz et al. | |
| 2012/0123184 A1 | 5/2012 | Otto et al. | |
| 2013/0090549 A1 | 4/2013 | Meltsner et al. | |
| 2018/0289980 A1* | 10/2018 | Fredriksson | A61N 5/1037 |
| 2019/0126064 A1* | 5/2019 | Flynn | A61N 5/1027 |
| 2019/0275352 A1 | 9/2019 | Deblois et al. | |
| 2021/0138264 A1* | 5/2021 | Isola | A61N 5/103 |
| 2021/0138266 A1* | 5/2021 | Isola | A61N 5/1031 |
| 2021/0220671 A1* | 7/2021 | Eriksson | A61N 5/1037 |
| 2022/0072334 A1* | 3/2022 | Fredriksson | A61N 5/103 |
| 2022/0241611 A1* | 8/2022 | Bokrantz | A61N 5/1031 |
| 2023/0023987 A1* | 1/2023 | Welsh | A61K 31/7076 |
| 2023/0115222 A1* | 4/2023 | Traneus | A61N 5/1043 600/1 |
| 2023/0141197 A1* | 5/2023 | Andersson | A61N 5/1031 600/1 |
| 2023/0144962 A1* | 5/2023 | Andersson | A61N 5/103 378/65 |
| 2023/0158334 A1* | 5/2023 | Lofman | A61N 5/103 600/1 |
| 2023/0302298 A1* | 9/2023 | Bengtsson | A61N 5/1038 |

FOREIGN PATENT DOCUMENTS

| | | |
|---|---|---|
| EP | 3081262 A1 | 10/2016 |
| EP | 3539616 A1 | 9/2019 |
| JP | 2017500165 A | 1/2017 |
| JP | 2019510585 A | 4/2019 |
| WO | 2018053648 A1 | 3/2018 |
| WO | 2018167324 A1 | 9/2018 |
| WO | 2018224623 A1 | 12/2018 |
| WO | 2019238602 A1 | 12/2019 |

OTHER PUBLICATIONS

International Search Report & Written Opinion, European Patent Office, Jun. 8, 2021, Rijswijk, Netherlands.
Office Action dated Dec. 3, 2024 in corresponding Japanese patent application No. 2022-558250, Japan Patent Office, Tokyo, Japan.

* cited by examiner

COMPUTER-IMPLEMENTED METHOD FOR RADIOTHERAPY TREATMENT PLANNING, COMPUTER PROGRAM PRODUCT AND COMPUTER SYSTEM FOR PERFORMING THE METHOD

TECHNICAL FIELD

The present invention relates to a computer-implemented method for radiotherapy treatment planning, and to a computer program product and an apparatus for carrying out such a method. In particular, the invention relates to treatment planning for radiotherapy that involves both external beam radiation therapy and brachytherapy for the same patient.

BACKGROUND

Most radiotherapy treatment is provided as external radiation that is delivered to a patient from an external source, known as external beam radiotherapy or EBRT. This is normally delivered in a number of fractions, for example, 15, 30 or more fractions. Alternatively, radiation may be delivered from a source that is placed within the patient. This is known as brachytherapy and involves placing one more needles or other type of equipment within the target in the patient to expose it to radiation from within. This is normally performed in a smaller number of fractions, for example, 1 or 3.

For EBRT treatment, planning is currently mostly performed as an inverse planning process in an optimization treatment planner. The aim is normally to achieve a minimum dose, or an even dose, over the whole target. Brachytherapy or BT planning requires the placement of equipment for providing radiation within the target, either physically or in a virtual environment and the dose is normally developed in a forward planning process in which the positions of the equipment and the dose resulting from it is determined. In low dose rate BT, one or more sources, known as seeds, are implanted into the target, and normally remain there for the foreseeable future. On the other hand, in high dose rate BT and pulsed dose rate BT, the radiation is delivered by radioactive sources moving through hollow channels in the implanted equipment, which consists of e.g. needles, catheters and applicators. Normally, the BT dose distribution is not uniform but is instead concentrated around the implanted equipment.

It is known in the art to combine EBRT and brachytherapy in the same patient. Typically, the EBRT fractions are delivered first and then the brachytherapy, but the opposite order is also possible. During the first treatment, the patient geometry will normally change. Also, the equipment inserted into the patient for brachytherapy will change the shape of the target and the surrounding tissue. For both these reasons, the two modalities will be delivered to different patient geometries. In the cases where both brachytherapy and external radiation treatment are used on the same patient, traditionally two separate treatments plans are developed, one for the EBRT portion of the treatment, and one for the brachytherapy portion of the treatment. These are typically based on a total dose and a predetermined division of the dose between the different types of treatment. For example, a total dose of 80 Gy may be set, where EBRT treatment is to contribute 60 Gy and brachytherapy the remaining 20 Gy. D1 discloses a radiotherapy treatment planning method allowing the combination of two or more modalities, which may include a combination brachytherapy and external beam radiation therapy. According to D1, the plan is optimized iteratively, first selecting and optimizing the most promising modality and then adding another modality and optimizing the contribution of this other modality.

It is an object of the present invention to provide an improved planning method for a treatment plan involving both EBRT and brachytherapy.

SUMMARY OF THE INVENTION

The invention relates to a computer-based method of optimizing a radiotherapy treatment plan for a patient, comprising the following steps
  a. obtaining input data comprising a first image of the patient,
  b. obtaining an optimization problem comprising an objective function designed to optimize a total dose distribution based on the input data as a combination of a first dose distribution to be provided by a first radiation set and a second dose distribution to be provided by a second radiation set based on dose criteria for the total dose distribution, wherein one of the radiation sets is external beam therapy and the other is brachytherapy,
  c. optimizing the treatment plan as a combination of external beam therapy and brachytherapy by means of the optimization problem.

Hence, according to the invention, the treatment parameters of the two radiation sets are optimized simultaneously by a joint optimization problem. This results in a better overall treatment plan than the separate planning according to the prior art. The first and the second dose may be delivered in any suitable order, or interleaved. The input data may also comprise a second image of the patient, which may be an estimated image of the patient after a portion of the treatment plan has been delivered. The second image may then be used to provide information about the patient's anatomy after the delivery of the portion. Typically, this portion is the portion to be delivered by the first radiation set.

Preferably, the method comprises the further step of, after delivery of a first portion of the treatment plan, determining the dose delivered to the patient, providing at least one updated image of the patient and optimizing the remaining treatment plan again using a second optimization problem taking into account the delivered dose and the updated image. This enables the remaining portion or portions of the treatment plan to be refined based on the actual result of the delivery of the first portion. The first portion typically corresponds to the dose delivered by the first radiation set and the remaining portion typically corresponds to the dose delivered by the second radiation set.

In some embodiments, the first portion of the treatment plan is the portion to be delivered as external beam therapy. In this case, the at least one updated image preferably comprises an updated image of the patient and an updated image of the patient with brachytherapy equipment applied, to take into account the actual patient geometry including brachytherapy equipment during delivery. The remaining treatment plan is updated based on the updated images.

In other embodiments, the first portion of the treatment plan is the portion to be delivered as brachytherapy. Preferably in such cases, step b is performed additionally based on a current image of the patient with brachytherapy equipment applied, to take into account the actual patient geometry during delivery.

The at least one updated image may comprise at least one image taken of the patient after delivery of the first portion. This will provide the most correct information on the actual patient geometry.

Alternatively, or in addition, the at least one updated image may comprise at least one simulated image based on an estimate of patient's geometry after delivery of the portion. This is suitable if, for some reason, it is not feasible to take a new image of the patient after delivery of the portion, or with the brachytherapy equipment inserted.

In preferred embodiments, the optimization comprises deforming at least one of the doses delivered by the first and second radiation set, respectively, to obtain a common geometry for the treatment portions and accumulating them using a biological model, the objective function being a set of penalties on the accumulated doses and on the radiation set-specific doses.

Preferably, robust planning is used to take into account uncertainties in the placement of brachytherapy equipment, in the EBRT delivery, and/or in determined delivered dose. how to implement robust planning is known in the art.

The invention also relates to a computer program product comprising computer-readable code means, which when run in a computer is arranged to make the computer perform a method according to any of the embodiments above. The computer program product may be stored on any suitable type of non-transitory storage medium.

The invention also relates to a computer system comprising a processor and at least one program memory, characterized in that the program memory holds a computer program as defined above.

In preferred embodiments, the invention involves planning of brachytherapy planning in which the accumulated dose already delivered to the patient by some other modality is also taken into account. This means that deviations from the planned dose to the target may be compensated for, but also that a too high dose to an organ at risk may be compensated for by changing the brachytherapy treatment plan accordingly.

BRIEF DESCRIPTION OF DRAWINGS

The invention will be described in more detail in the following, by way of examples and with reference to the appended drawings, in which.

DETAILED DESCRIPTION OF EMBODIMENTS

External beam radiation treatment, EBRT, involves providing radiation to the patient in the form of a beam delivered from the outside. The radiation may be any type of radiation, including photons, electrons, protons or other ions. Brachytherapy, BT, involves the insertion of some type of equipment into the target within the patient, and using said equipment to provide the radiation from one or more points within the target. This equipment may include a number of small needles and/or catheters, one or more larger applicators, one or more seeds, or any combination of the different types of equipment. Depending on the number and size of the devices, the target as well as the surrounding patient geometry will be deformed.

Due to the different natures of the two radiation sets, the planning of EBRT and BT use different treatment parameters. Treatment parameters for EBRT treatment include beam and beam limiting device configurations. Treatment parameters for BT treatment include variables such as equipment position and dwell times. Each radiation set typically involves radiation being delivered in one or more fractions, typically but not necessarily, a higher number for EBRT than for BT, which may even be delivered in one single fraction.

As discussed above, inverse planning using an optimization problem is common for EBRT planning but is not traditionally used for brachytherapy. The dose distribution EBRT could be expressed as $$d_{EBRT} = d_{EBRT}(x_{EBRT}) \tag{1}$$

and the dose distribution for brachytherapy could be expressed as $$d_{BT} = d_{BT}(x_{BT}) \tag{2}$$

where $x_{EBRT}$, $x_{BT}$ are treatment parameters for the respective treatment form.

The invention relates to simultaneous optimization of the treatment parameters for EBRT treatment and BT treatment. This means that the optimization problem can be expressed as Eq. (3)

$$\min_{x_{EBRT}, x_{BT}} f(d_{EBRT}, d_{BT}) \tag{3}$$

where $x_{EBRT}$ are the treatment parameters for the EBRT subportion of the treatment and $x_{BT}$ are the treatment parameters for the BT subportion of the treatment. $d_{EBRT}$ and $d_{BT}$ are the doses for the EBRT subportion and the BT subportion, respectively. Instead of the dose d, some other parameter related to the respective subportion may be used.

Typically, the optimization includes deforming the doses to a common geometry and accumulating them using a biological model, the objective function being a set of penalties on the accumulated doses and on the radiation set-specific doses.

Figure 1A:
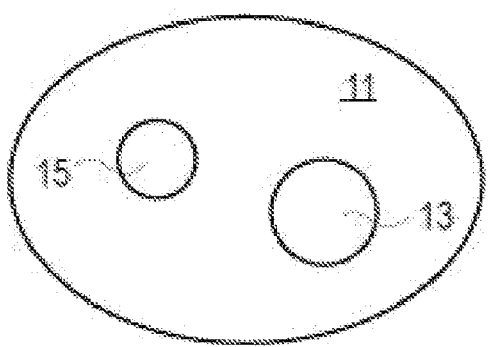
FIGS. 1a, 1b and 1c are sections through a medical image of a patient.
Figure 1B:
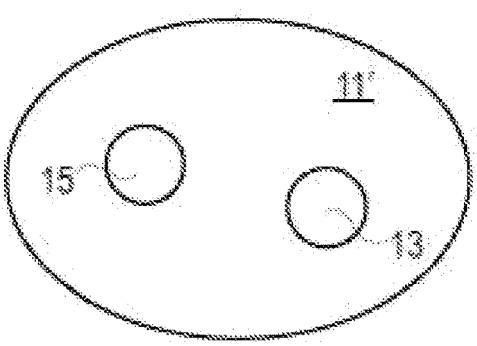
Figure 1C:
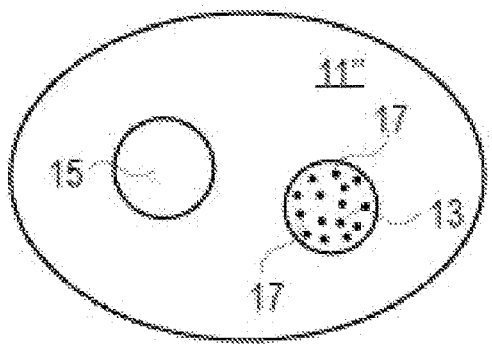

FIGS. 1a, 1b and 1c are simplified examples of medical images taken at different points in the inventive procedure, as will be discussed in more detail in connection with FIG. 2. FIG. 1a is a section 11 through a schematical medical image of a patient's abdomen, with a target 13 and an organ at risk 15 pointed out, to be used for treatment planning according to embodiments of the invention. FIG. 1b is a corresponding section 11' through a medical image of the same patient after a first type of treatment, illustrating schematically the changes that this treatment may have caused to the patient's geometry. As will be understood, the target 13 has shrunk because of the treatment, which is usually the desired result. FIG. 1c is the corresponding section 11" of a medical image of the same patient with needles inserted into the target for providing brachytherapy to the patient. The needles are shown as small dots 17 within the target. As can be seen, this also changes the geometry of the target 13" and of the region of the patient surrounding the target.

Figure 2:
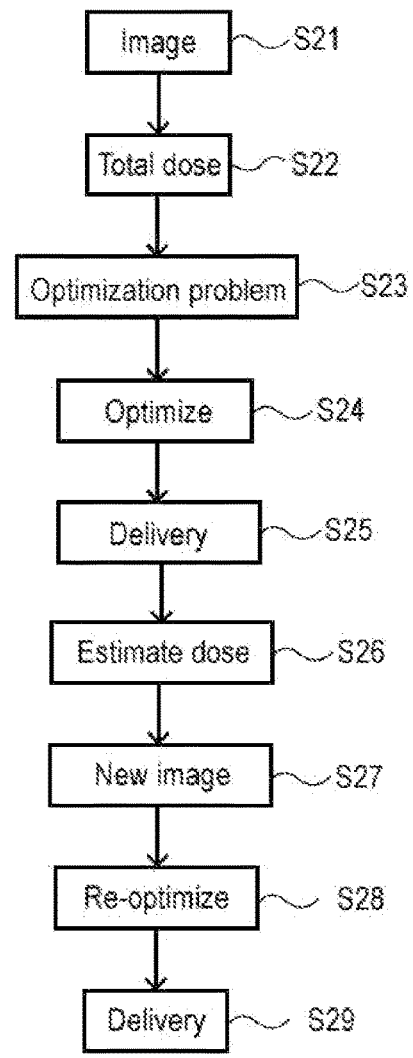
FIG. 2 is a flow chart of an general embodiment of the method.

FIG. 2 is a flow chart of an overall method according to an embodiment of the invention.

In a first step S21, an image of relevant portion of the patient, such as the one discussed in connection with FIGS. 1a-1c is obtained. In step S22, dose criteria for a total dose distribution to be delivered as a combined plan including both EBRT and brachytherapy is determined.

In step S23, the optimization problem is defined, based on the image or images and dose criteria for the desired total dose. Dose criteria are set as common in the art. They typically include a minimum dose for all voxels of the target and often a maximum dose for one or more organs at risk. For example, the dose criteria may specify a total dose of at least 60 Gy in each target voxel, and that at most 30% of an organ at risk is subjected to a total dose of more than 40 Gy. Dose criteria may also include a partial or complete dose distribution. In S24 the treatment plan is optimized using the optimization problem. The optimization problem includes an objective function such as function (3) above.

In step S25, a part of the treatment plan is delivered to the patient and in step S26 the accumulated dose delivered to the patient from the part of the treatment plan is estimated. The accumulated dose may be determined in any suitable way. Methods of doing this are well known in the art and are typically based on at least one medical image, for example a number of fraction images taken throughout the delivery of the first portion of the treatment plan.

In step S27, a new image of the same portion of the patient is obtained, to see the new patient geometry after the partial delivery in step S25. If applicable, other modifications may be made, such as the insertion of brachytherapy equipment and an image reflecting the resulting geometry may be taken. The new image may be an image taken of the patient at this stage, or a synthetic image based on estimates of the new patient geometry.

In step S28 the remainder of the treatment plan is optimized again, using an inverse planning method based on an optimization function that will be discussed in more detail below. The planning takes into account the accumulated dose of the partial delivery that has been performed previously. The optimization problem should then include an objective function according to the following:

$$\min_{x_{RS2}} g(d_{RS1}^{delivered}, d_{RS2}) \quad (4)$$

where $d_{RS1}^{delivered}$ is the delivered dose from the first radiation set, determined in step S26 and $d_{RS2}$ is the dose to be delivered by the second radiation set, and one of RS1 and RS2 is EBRT and the other one is BT.

where g is another objective function, which may or may not be equal to f and the delivered dose from the first radiation set over all fractions (either measured or estimated) is used a as a fixed background dose for the planning for the second radiation set.

In step S28, the reoptimized remainder of the plan is delivered to the patient.

Figure 3:
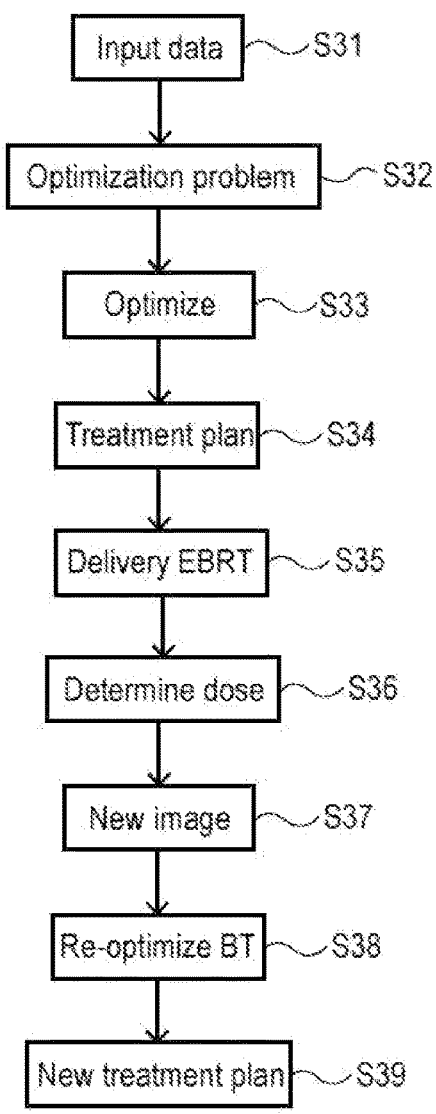
FIG. 3 is a flow chart of a more specific embodiment of the method including EBRT followed by BT.

FIG. 3 is a flow chart of an embodiment of the inventive method in which the total treatment plan includes first EBRT treatment and then BT treatment. The input data S31 to this plan include a current medical image of the patient, dose criteria for a desired dose distribution, and a prediction model of the patient geometry after the EBRT treatment. The prediction model may be an adjusted or synthetic medical image. The input data may also include a prediction model of the patient geometry after the EBRT treatment with the EB equipment included. The medical images may be CT images, or any other suitable image modality, such as MR or ultrasound images.

In a method step S32 the optimization problem is obtained based on the dose criteria and the input data. The optimization problem includes an objective function according to Eq. (3) based on the total dose of both the EBRT and the BT subportions of the treatment, and optionally the dose to be delivered for each radiation set. This typically includes deforming at least one of the doses $d_{EBRT}$ and $d_{BT}$ to a common geometry and accumulating them using a suitable biological model. This may include setting a combination of penalties on the accumulated doses and on the specific doses. Models for establishing a common geometry are known, typically including deformable registration of the images. Models for determining the accumulated dose are also known to the skilled person. For example, the biological concept EQD2 may be applied to give an estimate of the total effective dose.

In a subsequent method step S33, optimization is performed based on the common geometry and accumulated dose. The optimization problem includes an objective function according to Eq. (3) above. As will be understood, the objective function could also be extended to depend on the treatment parameters and the optimization problem may also include constraints depending on dose or treatment parameters. The output S34 from the optimization step S33 is a total treatment plan including one subportion for each radiation set, that is one EBRT subportion and one BT subportion. Each subportion includes the portion of the dose to be delivered by the corresponding radiation set and the number of fractions in which to deliver it.

The EBRT subportion of the treatment plan is then delivered to the patient, in a step S35 and the actual delivered dose from this delivery is determined or estimated in a step S36. Preferably, the situation after the EBRT delivery is assessed and used to refine the BT subportion of the treatment plan as outlined in the following steps.

In step S37, updated images of the patient after the EBRT treatment are obtained. These include a new image of the patient to account for the geometric changes that occurred during EBRT treatment. It also includes an image of the patient with the BT equipment inserted, since the BT equipment will cause an amount of deformation of the target and the surrounding patient geometry depending on the type of equipment.

In a subsequent step S38, the BT subportion of the treatment is reoptimized taking into account the delivered dose from step S35 and the new images obtained in step S37. The optimization problem in this case includes an objective function expressed as Eq. (2) below:

$$\min_{x_{BT}} g(d_{EBRT}^{delivered}, d_{BT}) \quad (5)$$

where $d_{EBRT}^{delivered}$ is the delivered dose determined in step S35.

The output from step S38 is a new optimized BT treatment plan S39, which is preferably delivered to the patient.

As discussed for FIG. 2, the steps S36-S39 may be performed without first performing the preceding steps, that is, the BT plan may take previous EBRT treatment into account even if there was no initial combined planning of the two.

Figure 4:
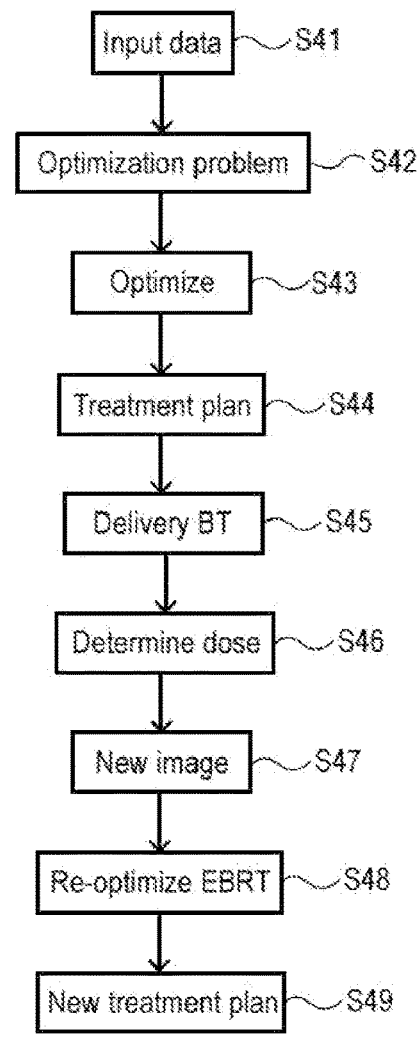
FIG. 4 is a flow chart of a second more specific embodiment of the method including BT followed by EBRT.

FIG. 4 is a flowchart of a method in which the first radiation set to be delivered is the BT. The input data S41 to this plan include a current medical image of the patient, and a medical image of the patient with the BT equipment inserted, and dose criteria for a desired dose distribution. Preferably, the input data also include a prediction model of the patient geometry after the BT treatment. The medical images may be CT images, or any other suitable image modality, such as MR or ultrasound images.

In a method step S42 the optimization problem is defined in a manner similar to step S32. When the BT dose portion is delivered first, the image of the patient with the BT equipment inserted is already available as input. These images can be deformably registered to provide a geometric correspondence between the treatment geometries. As in step S32, the doses $d_{EBRT}$ and $d_{BT}$ are deformed to a common geometry and accumulated using a suitable biological model. This may include setting a combination of penalties on the accumulated doses and on the specific doses. Models for establishing a common geometry are known, typically including deformable registration of the images. Models for determining the accumulated dose are also known to the skilled person.

In a subsequent method step S43, optimization is performed based on the common geometry and accumulated dose. The optimization problem includes an objective function according to Eq. (3) above. As will be understood, the optimization problem could also be extended to depend on the treatment parameters and also include other objective functions and/or constraints. The output S44 from the optimization step S43 is a total treatment plan including one subportion for each radiation set, that is one BT subportion and one EBRT subportion.

The BT subportion of the treatment plan is then delivered to the patient, in a step S45, and the actual delivered dose from this delivery is determined or estimated in a step S46. Preferably, the situation after the BT delivery is assessed and used to refine the EBRT subportion of the treatment plan as outlined in the following steps.

In step S47, an updated image of the patient after the BT treatment is obtained, to account for the geometric changes that occurred during BT treatment.

In a subsequent step S48, the EBRT subportion of the treatment is reoptimized taking into account the delivered dose from step S45 and the new image obtained in step S47. The optimization problem in this case includes an objective function expressed as Eq. (2) below:

$$\min_{x_{BT}} g(d_{BT}^{delivered}, d_{EBRT}) \qquad (6)$$

where $d_{BT}^{delivered}$ is the delivered dose determined in step S45.

The output from step S48 is a new optimized EBRT treatment plan S49, which is preferably delivered to the patient.

As discussed for FIGS. 2 and 3, the steps S46-S49 may be performed without first performing the preceding steps, that is, the EBRT plan may take previously delivered BT treatment into account even if there was no initial combined planning of the two.

It would also be possible to create a plan where the BT and EBRT fractions were not given as two consecutive sub-portions and instead the BT fractions were distributed between the EBRT fractions. In this type of treatment, the subportion or subportions of the treatment that have not yet been delivered can be reoptimized taking into account the delivered dose. Both the delivered and the nondelivered subportion of the treatment will typically be a combination of BT and EBRT. The optimization in this case includes an objective function expressed as Eq. (7) below $$\min_{x_{EBRT}x_{BT}} g(d_{BT}^{delivered}, d_{EBRT}^{delivered}, d_{BT}, d_{EBRT}) \qquad (7)$$

In all of the above methods, the simultaneous optimization should be performed with some care, to ensure that the individual doses of each radiation set are still satisfactory on their own. One possible adverse effect of co-optimization would be an EBRT dose with cold spots in the targets that are to be later filled in by the BT dose. This could mitigated by incorporating robustness into the model against e.g. the uncertainty of equipment positioning and the deforming effect of the equipment. Treatment-specific objective functions are also a possibility (analogously to the current beam set-specific objective functions).

As with any radiotherapy treatment planning there will be sources of uncertainty, including the placement of the patient, the positioning of the BT equipment and the estimated delivered dose. To compensate for this, robust planning may be used. In particular, the deformation between the images will result in an approximate accumulated dose, the quality of which depends on the accuracy of the deformable registration. To avoid over-optimizing on an accumulated dose that differs from the dose that will actually be delivered, methods for robust planning over a representation of the uncertainty could be employed. Various degrees of refinement could be used, for example:

- Margins could be applied, as an ITV over predicted images, or just smearing of the regions to be treated.
- Robust planning using scenarios generated as rigid shifts of the patient geometry, may be applied, independently for each of the radiation sets.
- Robust planning using scenarios generated by multiple deformable registrations could be applied. In the case where the EBRT partial dose is delivered before the BT partial dose, this would involve utilizing multiple predictions. In the case where the BT partial dose is delivered before the EBRT partial dose, this would involve or using perturbations of the registrations between the acquired images. The deformations can also come from anatomical changes during EBRT, e.g. tumor shrinkage.

The method according to embodiments of the invention may also be combined with multi-criteria optimization. In this case the navigation could take place on several fronts, with several trade-off objectives targeting either the total dose or either of the individual treatment doses.

Figure 5:
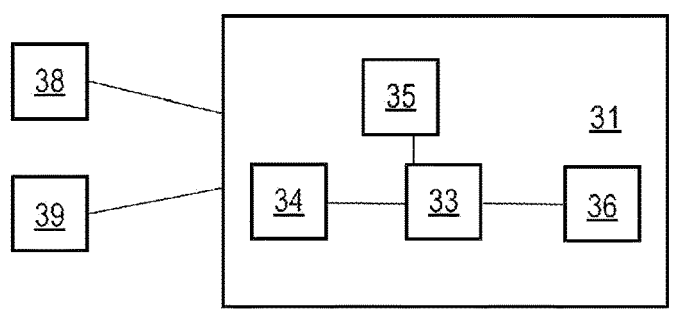
FIG. 5 is a schematic overview of a computer system in which embodiments of the invention may be implemented

FIG. 5 is a schematic representation of a computer system in which the inventive method may be performed. A computer 31 comprises a processor 33, connected to a first and a second data memory 34, 35 and a program memory 36. Preferably, one or more user input means 38, 39 are also present, in the form of a keyboard, a mouse, a joystick, voice recognition means or any other available user input means. The user input means may also be arranged to receive data from an external memory unit.

The first data memory 34 comprises necessary data for performing the method, such as the necessary images. The second data memory 35 holds data related to one or more current patients for which treatment plans are to be developed. The program memory 36 holds a computer program arranged to make the computer perform the method steps, for example, as discussed in connection with any of the FIGS. 2, 3 and 4.

As will be understood, the data memories 34, 35 as well as the program memory 36 are shown and discussed schematically. There may be several data memory units, each holding one or more different types of data, or one data memory holding all data in a suitably structured way, and the same holds for the program memories. One or more of the components may be found in a cloud environment, as long as the components are able to communicate with each other.

The invention claimed is:

1. A computer-based method of optimizing a radiotherapy treatment plan for a patient, comprising the following steps:
   a. obtaining input data comprising a first image of the patient,
   b. obtaining an optimization problem comprising an objective function designed to optimize a total dose distribution based on the input data as a combination of a first dose distribution to be provided by a first radiation set and a second dose distribution to be provided by a second radiation set based on dose criteria for the total dose distribution, wherein one of the radiation sets is external beam therapy and the other is brachytherapy, and
   c. optimizing the treatment plan as a combination of external beam therapy and brachytherapy by means of the optimization problem, wherein the optimization comprises deforming the doses to a common geometry and accumulating them using a biological model, the objective function being a set of penalties on the accumulated doses and on the radiation set-specific doses.

2. The method of claim 1, wherein the input data further comprises a second image of the patient.

3. The method of claim 2, wherein the second image is an estimated result image of the patient after a portion of the treatment plan has been delivered.

4. The method of claim 1, further comprising the steps of
   d. after delivery of a first portion of the treatment plan, determining the dose delivered to the patient, providing at least one updated image of the patient and optimizing the remaining treatment plan again using a second optimization problem taking into account the delivered dose and the updated image.

5. The method of claim 4, wherein the first portion of the treatment plan is the portion to be delivered as external beam therapy, the at least one updated image comprising an updated image of the patient and an updated image of the patient with brachytherapy equipment applied, and optimizing the remaining treatment plan based on the updated images.

6. The method of claim 4, wherein the first portion of the treatment plan is the portion to be delivered as brachytherapy, step b is performed additionally based on a current image of the patient with brachytherapy equipment applied.

7. The method of claim 4, wherein the at least one updated image comprises at least one image taken of the patient after delivery of the portion.

8. The method of claim 4, wherein the at least one updated image comprises at least one simulated image based on an estimate of patient's geometry after delivery of the portion.

9. The method of claim 1, wherein robust planning is used to take into account uncertainties in the brachytherapy delivery, in the EBRT delivery, and/or in determined delivered dose.

10. A computer program product comprising a non-transitory computer readable storage medium having program instructions embodied therewith, which when run in a computer are arranged to make the computer perform a method according to claim 1.

11. A computer system comprising a processor and at least one program memory, wherein the program memory holds a computer program product according to claim 10.

* * * * *